(12) United States Patent
Betsinger et al.

(10) Patent No.: US 8,997,792 B2
(45) Date of Patent: Apr. 7, 2015

(54) ABRASION MONITORING SYSTEM FOR HOSE ASSEMBLY

(71) Applicant: Eaton Corporation, Cleveland, OH (US)

(72) Inventors: James Betsinger, Waterville, OH (US); Mike Beining, Maumee, OH (US); Mike Wells, Bowling Green, OH (US)

(73) Assignee: Eaton Corporation, Cleveland, OH (US)

( * ) Notice: Subject to any disclaimer, the term of this patent is extended or adjusted under 35 U.S.C. 154(b) by 0 days.

(21) Appl. No.: 13/930,986

(22) Filed: Jun. 28, 2013

(65) Prior Publication Data

US 2014/0000742 A1 Jan. 2, 2014

Related U.S. Application Data

(60) Provisional application No. 61/666,392, filed on Jun. 29, 2012.

(51) Int. Cl.
| | | |
|---|---|---|
| *F16L 11/127* | (2006.01) | |
| *F16L 57/06* | (2006.01) | |
| *G01N 27/20* | (2006.01) | |
| *G01M 3/40* | (2006.01) | |

(52) U.S. Cl.
CPC .............. *F16L 57/06* (2013.01); *F16L 11/127* (2013.01); *G01N 27/20* (2013.01); *G01M 3/40* (2013.01)

(58) Field of Classification Search
USPC ................ 138/36, 104, 127, 143, 133, 109; 340/604; 324/71.1
See application file for complete search history.

(56) References Cited

U.S. PATENT DOCUMENTS

| | | | | | |
|---|---|---|---|---|---|
| 5,343,738 | A | * | 9/1994 | Skaggs | 73/40.5 R |
| 5,634,497 | A | * | 6/1997 | Neto | 138/127 |
| 5,969,618 | A | * | 10/1999 | Redmond | 340/604 |
| 6,498,991 | B1 | * | 12/2002 | Phelan et al. | 702/34 |
| 7,555,936 | B2 | * | 7/2009 | Deckard | 73/49.5 |
| 8,087,430 | B1 | * | 1/2012 | Betz et al. | 138/104 |
| 8,183,872 | B2 | * | 5/2012 | Stark | 324/539 |
| 2001/0018845 | A1 | | 9/2001 | Roberts | |
| 2006/0196252 | A1 | | 9/2006 | Deckard | |
| 2010/0007325 | A1 | | 1/2010 | Stark | |

OTHER PUBLICATIONS

Partial International Search Report for PCT/US2013/048660 mailed Mar. 24, 2014.
International Search Report and Written Opinion for PCT/US2013/048660 mailed Sep. 8, 2014.

* cited by examiner

*Primary Examiner* — Patrick F Brinson
(74) *Attorney, Agent, or Firm* — Merchant & Gould P.C.

(57) ABSTRACT

A system and method for detecting hose abrasion are disclosed. In one aspect, a hose abrasion monitoring system includes a hose assembly a monitoring circuit. The hose assembly includes a hose having at least one conductive layer and at least one outer insulating cover overlaying the at least one conductive layer. The monitoring circuit is in electrical communication with the at least one conductive layer. Upon abrasion of the at least one outer cover to expose a portion of the at least one conductive layer, the monitoring circuit is configured to detect electrical continuity between the at least one conductive layer and a conductive component external to the hose.

20 Claims, 7 Drawing Sheets

ABRASION MONITORING SYSTEM FOR HOSE ASSEMBLY

CROSS-REFERENCE TO RELATED APPLICATIONS

The present application claims priority from U.S. Provisional Patent Application No. 61/666,392, filed on Jun. 29, 2012, the disclosure of which is hereby incorporated by reference in its entirety.

BACKGROUND

High pressure reinforced hydraulic hose is typically used on a variety of fluid power operated machines, such as earth-moving machines, to provide a flexible connection between several moving parts of a hydraulic circuit employed on or within the machine. Such hoses may include a hollow polymeric inner tube on which successive cylindrical layers of reinforcing material, such as wire or textile, are concentrically applied to contain the radial and axial pressures developed within the inner tube.

Many applications are demanding hose constructions with both high burst strength and long term fatigue resistance. Using conventional technology, the burst strength of a hose design may be increased by adding additional reinforcing material and/or layers, a practice which is generally discouraged because of its negative impact on the flexibility of the hose, or by universally increasing the tensile strength of each layer of reinforcement material, which may come at the expense of hose fatigue resistance.

To determine the robustness of a hose design, a hose manufacturer typically performs, among other tests, an impulse test and a burst test on the hose. An impulse test measures a hose design's resistance to fatigue failure by cyclically subjecting the hose to hydraulic pressure. A burst test, on the other hand, is a destructive hydraulic test employed to determine the ultimate strength of a hose by uniformly increasing internal pressure until failure. Based on these and other tests, a manufacturer can estimate a hose life that can be used to determine when a hose has reached the end of its life and may require replacing.

In some circumstances, it is desirable to detect, in a non-destructive and non-disruptive manner a likelihood of failure of a hydraulic hose. One solution providing this capability is discussed in U.S. Pat. No. 7,555,936, and discloses connecting a monitor circuit between two parallel, at least partially-conductive layers of a hose wall. As noted in that patent, a change in an electrical property observed by that monitor circuit may indicate a change in a property of the hose wall structure that might indicate impending failure of the hose wall. However, such a structure with two parallel layers of a hose wall must be manufactured to a high tolerance, and is generally of a higher expense than may be warranted in some applications. For example, in the case where only abrasion is to be detected, an arrangement that monitors electrical characteristics of an inner layer of the hose is unnecessary. Furthermore, because abrasion failures represent a large number of the overall failures of a hydraulic hose (e.g., up to 80-90% of all failures), it may be important to account for abrasion-based failures, even where other types of failures are of less concern.

SUMMARY

In accordance with the following disclosure, the above and other issues are addressed by the following:

A first aspect of the present disclosure relates to a hose abrasion monitoring system. The system includes a hose assembly and a monitoring circuit. The hose assembly includes a hose having at least one conductive layer and at least one outer insulating cover overlaying the at least one conductive layer. The monitoring circuit is in electrical communication with the at least one conductive layer. Upon abrasion of the at least one outer cover to expose a portion of the at least one conductive layer, the monitoring circuit is configured to detect electrical continuity between the at least one conductive layer and a conductive component external to the hose.

A second aspect of the present disclosure relates to a method of monitoring abrasion of a hose assembly. The method includes applying a voltage across a monitoring circuit electrically connected between at least one conductive layer of the hose assembly and a conductive surface of a component, and measuring electrical continuity between the at least one conductive layer and the conductive surface. The at least one conductive layer may be electrically insulated from the conductive surface.

A third aspect of the present disclosure relates to a hose abrasion monitoring system. The hose abrasion monitoring system includes a hose assembly including a hose having a conductive layer and an outer insulating cover. The system also includes a fitting for fluidly connecting the hose and a component, the component having a conductive surface. The fitting includes a socket electrically connected to the conductive layer, and a nipple electrically connected to the conductive surface, the nipple being electrically insulated from the socket. The system further includes a monitoring circuit electrically connected between the nipple and the socket, and a diagnostic unit having a sensor measuring electrical continuity between the socket and the nipple.

DETAILED DESCRIPTION

Reference will now be made in detail to the exemplary aspects of the present disclosure that are illustrated in the accompanying drawings. Wherever possible, the same reference numbers will be used throughout the drawings to refer to the same or like structure.

Figure 1:
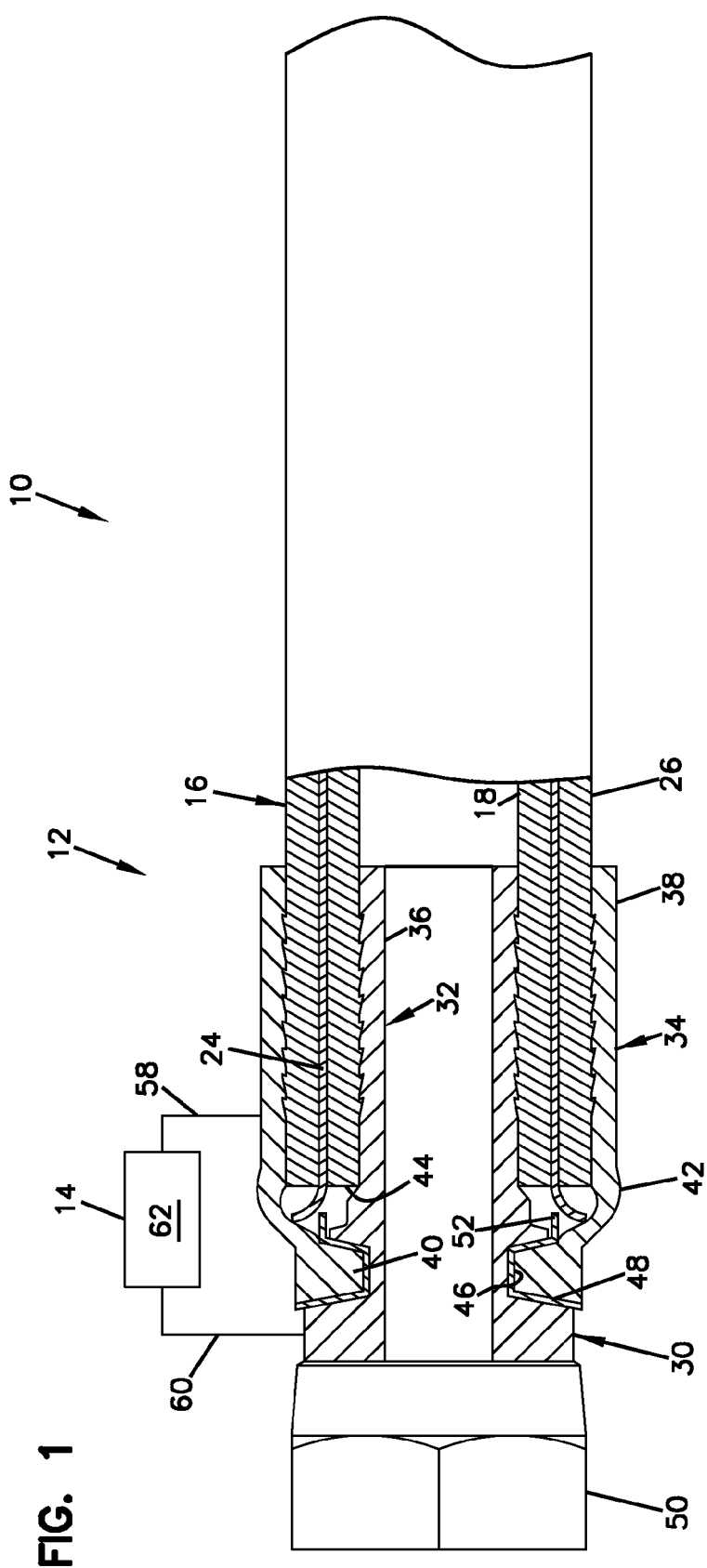
FIG. 1 is a partial cross-sectional view of an exemplary hose assembly employing an abrasion monitoring circuit having exemplary features of aspects in accordance with the principles of the present disclosure.

Referring now to FIG. 1, an exemplary hose abrasion monitoring system, generally designated 10, is shown. The hose abrasion monitoring system 10 includes a hose assembly, generally designated 12, and a diagnostic unit 14 in electrical and physical communication with the hose assembly 12.

The hose assembly 12 includes a hose, generally designated 16, having a multi-layer construction. In the subject embodiment, the hose 16 is generally flexible and includes an inner tube 18, a conductive layer 24 and an outer cover 26. The inner tube 18 may be made from a polymeric material, such as rubber or plastic, or another material depending on the requirements of the particular application. The conductive layer 24 defines an electrical characteristic of the hose assembly 12, such as capacitance, inductance and/or resistance (impedance).

In the embodiment shown, the conductive layer 24 overlays the inner tube 18. The conductive layer 24 may be configured as a reinforcing layer. The outer cover 26 may be configured as an insulating layer and overlay the conductive layer 24. The outer cover 26 may include, for example, an extruded layer of rubber or plastic. The outer cover 26 may itself include a reinforcing layer.

In the embodiment shown, the conductive layer 24 generally extends substantially the entire length and spans substantially the entire circumference of the hose. This is generally the case when the conductive layer also functions as a reinforcement layer. There may be an instance, however, where the conductive layer 24 extends only over a portion of the hose length and/or a portion of its circumference.

Figure 2:
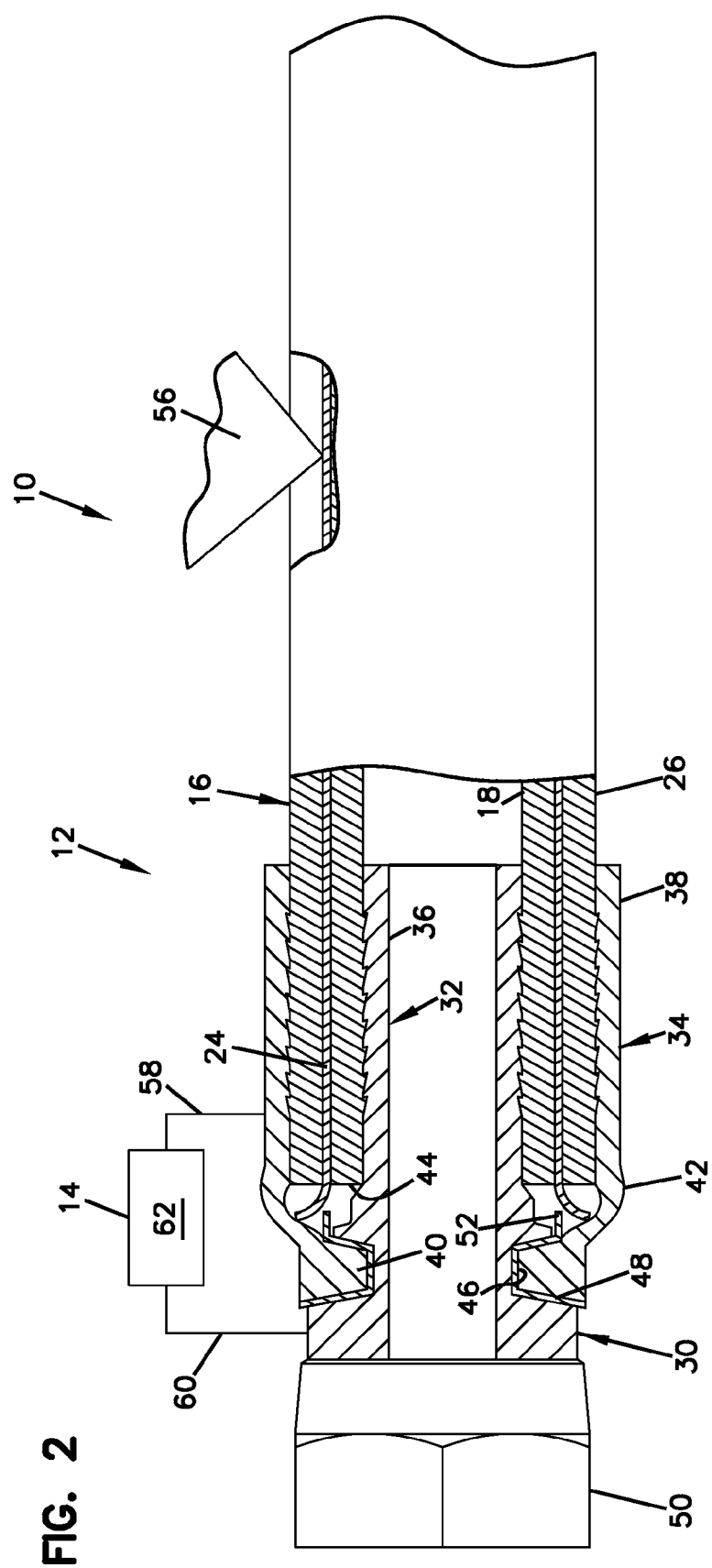
FIG. 2 is a partial cross-sectional view of the hose assembly of FIG. 1, illustrating the exposure of a conductive layer of the hose assembly by abrasion of the hose by an external component.

Referring to FIGS. 1 and 2, the hose assembly 12 may include a hose fitting, generally designated 30, for providing a fluidic coupling of the hose 16 to a component external to the hose assembly 12. The hose fitting 30 may have any of a variety of different configurations depending, at least in part, on the requirements of the particular application.

In the embodiment shown, the hose fitting 30 includes a nipple, generally designated 32, that engages the inside of the hose 16 and a socket, generally designated 34, that engages the outside of the hose 16. The nipple 32 includes an elongated cylindrical end portion 36 that engages the inner tube 18 of the hose 16. A cylindrically shaped end portion 38 of the socket 34 engages the outer cover of the hose 16. The socket 34 and nipple 32 may be constructed from an electrically conductive material.

The socket 34 and nipple 32 can be secured to the hose 16 by crimping the end portion 38 of the socket 34 overlaying the hose 16. The crimping process deforms the end portion 38 of the socket 34, thereby compressing the hose 16 between the nipple 32 and the socket 34. In the subject embodiment, the portions of the nipple 32 and the socket 34 that engage the hose 16 include a series of serrations that at least partially embed into the relatively softer hose material when the socket 34 is crimped to help secure the hose fitting 30 to the hose 16. The serrations may be configured to be prevented from penetrating the inner tube and outer cover and contacting the conductive layer 24. However, in some embodiments the serrations may penetrate the outer cover and contact the conductive layer. In such embodiments, the serrations, socket 34, and conductive layer 24 must nevertheless remain electrically isolated from the nipple 32.

In the embodiment shown, the socket 34 includes an inwardly extending circumferential lug 40 positioned near an end 42 of the socket 34 adjacent an end 44 of the hose 16. The lug 40 engages a corresponding circumferential slot 46 formed in the nipple 32 for securing the socket 34 to the nipple 32. The end 42 of the socket 34 having the lug 40 is initially formed larger than the nipple 32 to enable the socket 34 to be assembled onto the nipple 32. During the assembly process the end 42 of the socket 34 is crimped, which deforms the socket 34 and forces the lug 40 into engagement with the corresponding slot 46 in the nipple 32. The socket 34 can be electrically insulated from the nipple 32 by positioning an electrically insulating collar 48 between the socket 34 and nipple 32 at the point the lug 40 engages the slot 46.

The hose fitting 30 also includes a nut 50 rotatably attached to the nipple 32. The nut 50 provides a means for securing the hose assembly 12 to the component 54. The nut 50 may be constructed from an electrically conductive material, and may thus be electrically connected to the nipple 32 of the hose fitting 30 when attached to the nipple 32. As such, in this embodiment, the nut 50 remains electrically isolated from the socket 34.

The conductive layer 24 may be configured to extend beyond an end of the outer cover of the hose 16. The conductive layer 24 may engage the socket 34 to create an electrical connection between the socket 34 and the conductive layer 24. In alternative embodiments, serrations associated with (and electrically connecting to) the socket 34 may penetrate the outer cover of the hose 16, and contact the conductive layer 24 to establish electrical connection between the socket 34 and the layer 24.

To help prevent the portions of the conductive layer 24 that extends beyond the end of the hose 16 from contacting the nipple 32, an electrically insulating spacer 52 may be positioned between the nipple 32 and the exposed ends of the conductive layer 24. The spacer 52 may be integrally formed as part of the collar 48 used to electrically insulate the socket 34 from the nipple 32. The spacer 52 may also be configured as a standalone component separate from the collar 48.

In some applications, a component, such as a vehicle or other equipment requiring hydraulic connections, is coupled with the hose fitting 30. Such a component can have a body that is at least partially electrically conductive, such that it would be in electrical continuity with the nut 50 and the nipple 32, while remaining isolated from the socket 34. The component can include a conductive surface 56, for example as seen in FIG. 2, which may come into contact with an outer cover 26 of the hose during operation. The conductive surface 56 may include, without limitation, a vehicle bumper or guardrail, a trail, or, any other metallic surface of a piece of hydraulic equipment.

In some cases, and as further illustrated in FIG. 2, over time the surface 56 may cause abrasion of the outer cover 26, thereby wearing away the outer cover and exposing the conductive layer 24. In other words, the component 54 may be any type of equipment having a metallic surface extending from one portion of the equipment contacting the hose fitting 30 and the other portion contacting the outer cover 26 of the hose 16.

In accordance with the present disclosure, the diagnostic unit 14 is configured to detect the occurrence of such wear of the outer cover 26, generally by monitoring electrical continuity between portions of the hose assembly 12 that would during normal operation be electrically isolated. The diagnostic unit 14 can take any of a variety of forms. In general the diagnostic unit can include one or more microcontrollers, a power supply, and/or other circuitry useable to generate test signals capable of testing electrical continuity between the nipple 32 and socket 34, and generating an alarm if such electrical continuity is detected.

As seen in FIGS. 1-2, the diagnostic unit 14 may have any of a variety of structural configurations as well. In general, the diagnostic unit 14 is connectable over a portion of the hose assembly 12. The diagnostic unit 14, when installed over the hose assembly 12, forms a physical and electrical connection with the hose assembly 12, and in particular to the nipple 32 and the socket 34, respectively. Generally, the diagnostic unit 14 detects an electrical characteristic of the hose assembly 12, while validating the connection to the nipple 32 and the socket 34. In some embodiments, the diagnostic unit 14 includes a sensing device 62, which is configured to measure an electrical characteristic, such as resistance or some other characteristic, capable of indicating an existence of electrical continuity between the nipple 32 and the socket 34.

FIG. 2 illustrates a circumstance in which the outer cover 26 of the hose 16 is abraded by the surface 56 of the component. In this case, an exposed portion of the conductive layer 24 electrically contacts the surface 56 of the component. This contact allows the surface 56 and the conductive layer 24 to come into electrical contact, and thereby causes the nipple 32 and socket to have electrical continuity, due to the electrical connection between the surface 56 and the nipple, via the component. As such, the diagnostic unit 14 may detect such electrical continuity and indicate the abrasion of the hose 16, as described in detail below in reference to FIGS. 6 and 7.

Figure 3:
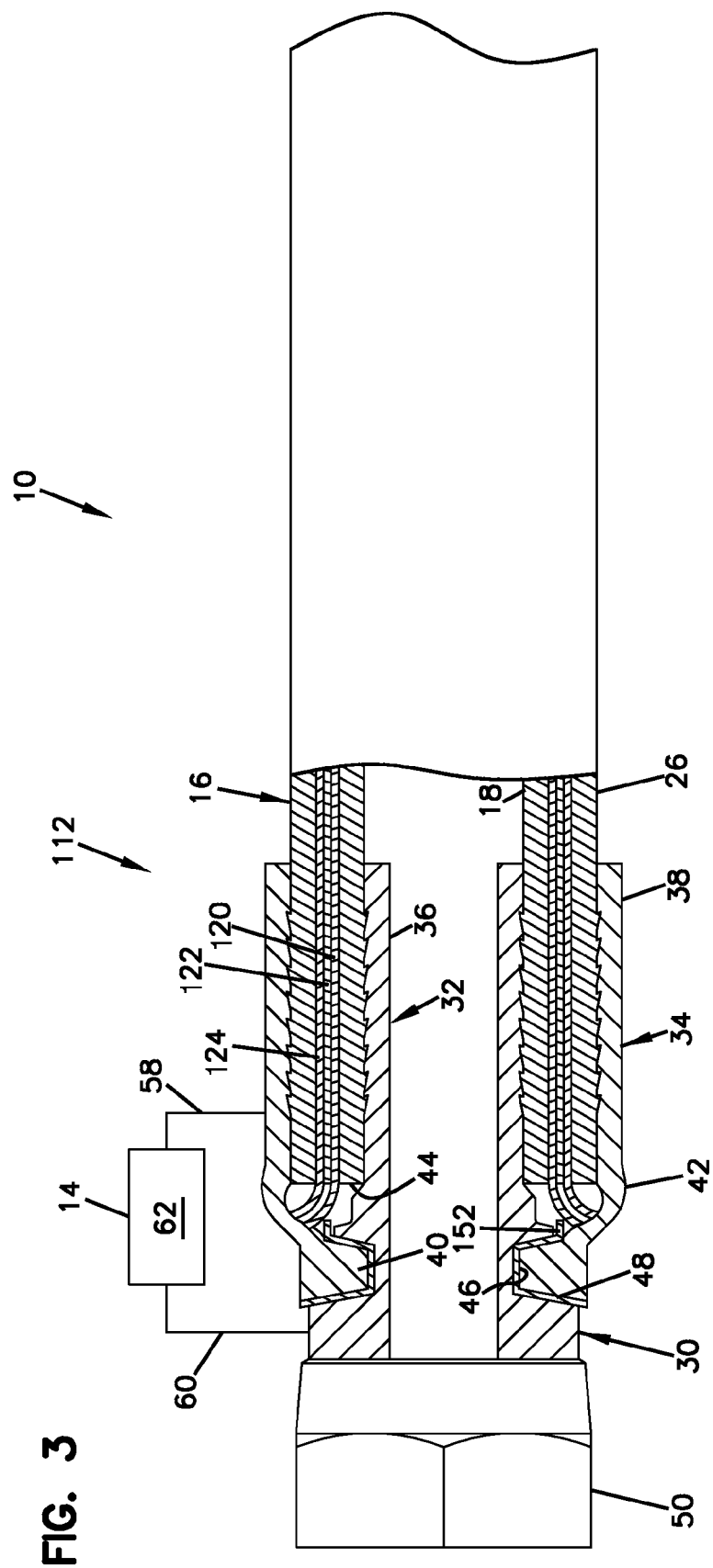
FIG. 3 is a partial cross-sectional view of an exemplary hose assembly employing an abrasion monitoring circuit having exemplary features of aspects in accordance with another exemplary embodiment of the present disclosure.

FIG. 3 illustrates an alternative embodiment of a hose assembly, generally designated 112. The hose assembly in this embodiment is substantially identical to the structure of the hose assembly 12, except two conductive layers and structures associated therewith. The same structures are, therefore, identified with the same reference numbers and their detailed explanations are omitted for brevity.

In this embodiment, the hose 16 includes a first conductive layer 120, an intermediate layer 122, a second conductive layer 124 and an outer cover 26. The first and second conductive layers 120, 124 define an electrical characteristic of the hose assembly 112, such as resistance.

The first conductive layer 120 overlays the inner tube 18 and the intermediate layer 122 overlays the first conductive layer 120. The second conductive layer 124 overlays the intermediate layer 122. The first and second conductive layers 120, 124 may be configured as reinforcing layers. The outer cover 26 may overlay the second conductive layer 124, and may include, for example, an extruded layer of rubber or plastic. The outer cover 26 may itself include a reinforcing layer.

In some embodiments in which two or more layers 120, 124 are present, an intermediate layer 122 operates to at least partially insulate electrically the first and second conductive layers 120, 124 from one another. The intermediate layer 122 may have any of a variety of constructions. For example, the intermediate layer 122 may consist of a single layer of an electrically resistive material. The intermediate layer 122 may also consist of multiple layers, with at least one of the layers exhibits electrical insulating properties. Certain composite materials may also be employed in the intermediate layer 122, such as a woven fabric bonded to a polymeric material. Composite materials having various other constructions may also be utilized. Composite materials may also be used in combination with other materials to form the intermediate layer 122. In alternative embodiments, the intermediate layer 122 may not completely electrically isolate layers 120, 124, or may not be present entirely. In general, only the outermost conductive layer (in this case, layer 120) is to be connected to the socket 34.

In the embodiment shown, the first and second conductive layers 120, 124 extend substantially the entire length and span the entire circumference of the hose. This is generally the case when the conductive layer also functions as a reinforcement layer. The intermediate layer 122 also extends substantially the entire length and circumference of the hose, and is present at least in all areas where first and second conductive layers 120, 124 are present. There may be instances, however, where at least one of the first and second conductive layers 120, 124 extends only over a portion of the hose length and/or a portion of its circumference. In that instance, the intermediate layer 122 may also be configured to generally extend over the region of the hose containing the partial conductive layer 120, 124.

The second conductive layer 124 may be configured to extend beyond the end of the outer cover of the hose 16. The second conductive layer 124 may engage the socket 34 to create an electrical connection between the socket 34 and the second conductive layer 124. Similarly, the first conductive layer 120 may be configured to extend beyond an end of the inner tube of the hose 16; however, electrical connection of any layer but an outermost conductive layer is not required.

In some embodiments, such as that shown, the first conductive layer 120 may also engage the socket 34 to create an electrical connection between the socket 34 and the first conductive layer 120. As such, the conductive layers 120, 124 are both connected to the socket 34. This structure is advantageous in cases where the second conductive layer 124 and the intermediate layer 122 are not reliably present. To help prevent the portions of the first and second conductive layers 120, 124 that extend beyond the end of the hose 16 from contacting the nipple 32, an electrically insulating spacer 152 may be positioned beneath the exposed end of the first conductive layers 120. The spacer 152 may be integrally formed as part of the collar 48 used to electrically insulate the socket 34 from the nipple 32. The spacer 152 may also be configured as a standalone component separate from the collar 48.

In alternative embodiments where an intermediate layer 122 is reliably present, the conductive layer 120 can be configured to contact the nipple 32 rather than the socket, such that electrical continuity changes can be detected in the event of either abrasion of the outer layer 16, or degradation of the intermediate layer 122. One example of this arrangement of layers of a hose is illustrated in copending U.S. patent application Ser. No. 13/458,691, the disclosure of which is hereby incorporated by reference in its entirety.

In still another embodiment, the first conductive layer 120 may engage neither the socket 34 nor the nipple 32 while the second conductive layer 124 engages the socket 34 to create an electrical connection with the socket 34. In this instance, the first conductive layer 120 does not create an electrical connection with the socket 34, and thus does not contribute the detection of abrasion of the hose 16. The second conductive layer 124 is only used to monitor abrasion of the hose 16 in the same way as in FIGS. 1 and 2 and their accompanying descriptions.

Figure 4:
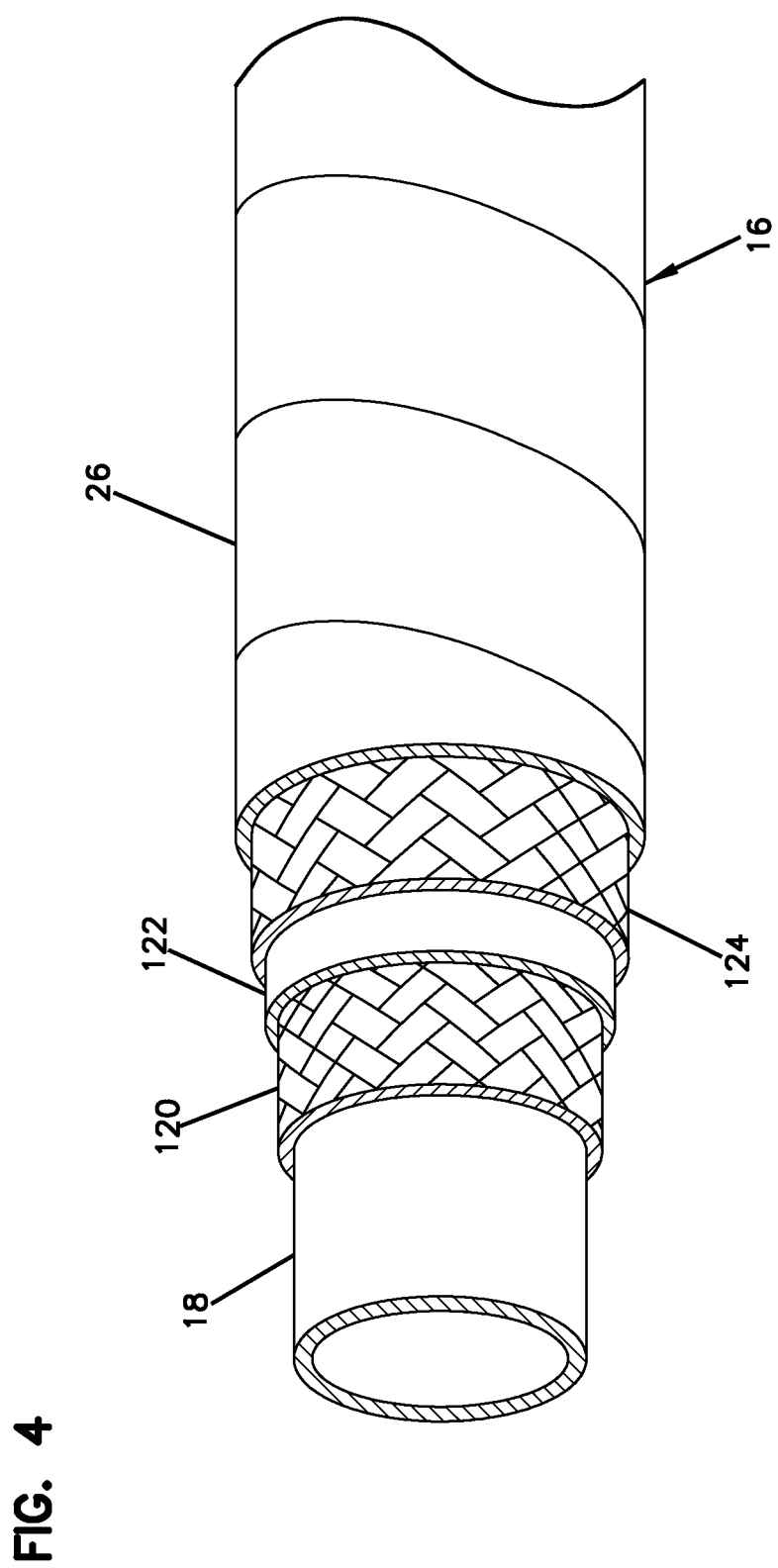
FIG. 4 is a perspective view, partially cut away, illustrating an exemplary hose employing a braided conductive layer that is suitable for use with the hose assembly of FIG. 3.
Figure 5:
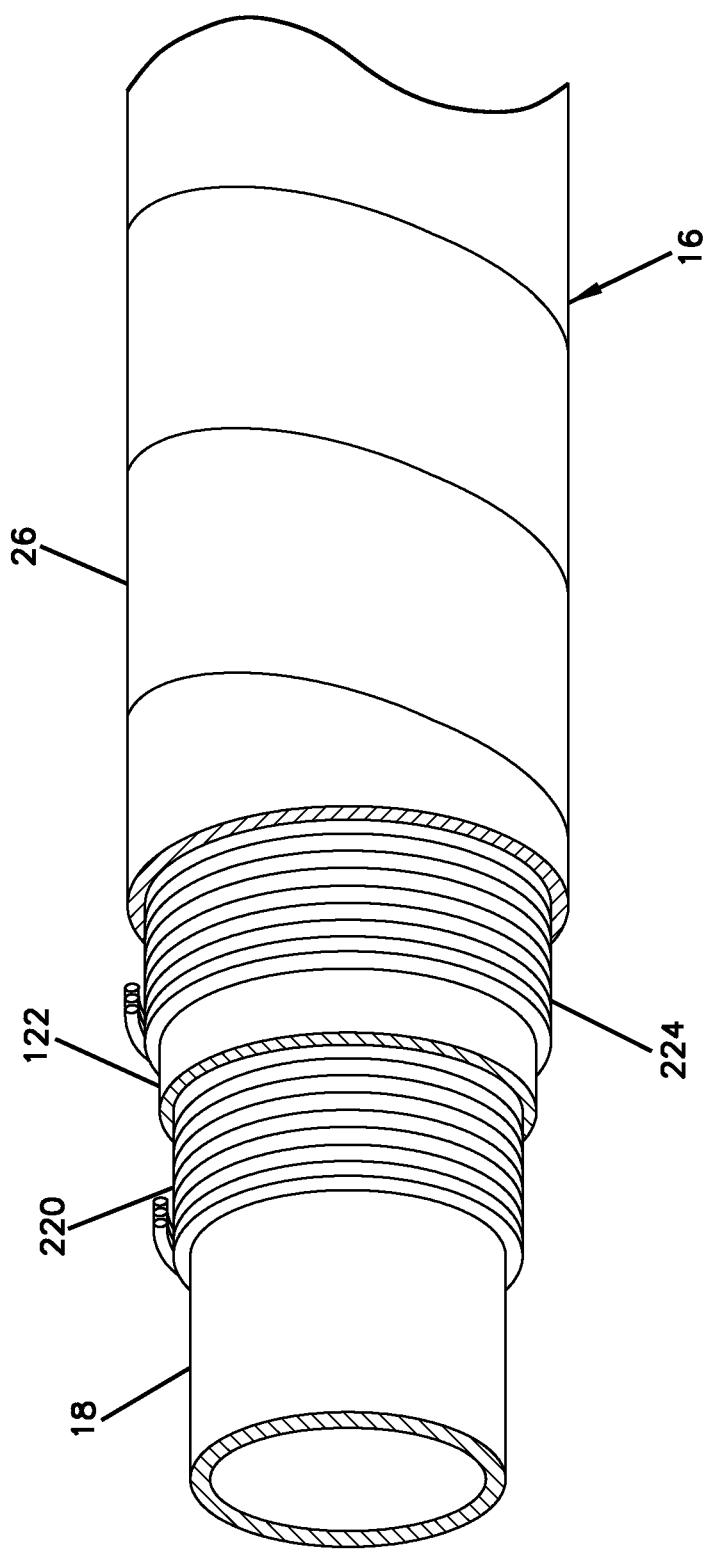
FIG. 5 is a perspective view, partially cut away, illustrating an exemplary hose employing a spiral wire conducting layer that is suitable for use with the hose assembly of FIG. 3.

Referring now to FIGS. 4-5, at least one of the exemplary conductive layers 24, 120, 124 may include, for example, an electrically conductive braided reinforcement material, such as shown in FIG. 4, or alternating layers of electrically conductive spiral reinforcement material, such as shown in FIG. 5. The braided reinforcement material may consist of a single layer or may include multiple layers. Although a two-wire spiral reinforcement arrangement is depicted in FIG. 5, it shall also be appreciated that other configurations, such as four and six wire arrangements, may also be utilized. Furthermore, additional conductive layers can be used, separated by corresponding insulating layers. An example of such a configuration is illustrated in PCT Publication No. WO 2010/0110941 A1.

In the structure illustrated in FIG. 3, the first and second conductive layers 120, 124 may each have the same configuration, or each layer may be configured differently. For example, the first and second conductive layers 120, 124 may each include the braided material shown in FIG. 4, or one of the first and second conductive layers 120, 124 may include the braided material while the other of the first and second conductive layers 120, 124 may include the spiral reinforcement material shown in FIG. 5. Additionally, the first and second conductive layers 120, 124 may include a single ply or multiple plies of reinforcement material. The first and second conductive layers 120, 124 may comprise metal wire, natural or synthetic fibers and textiles, and other reinforcement materials, provided the selected material is electrically conductive.

Figure 6:
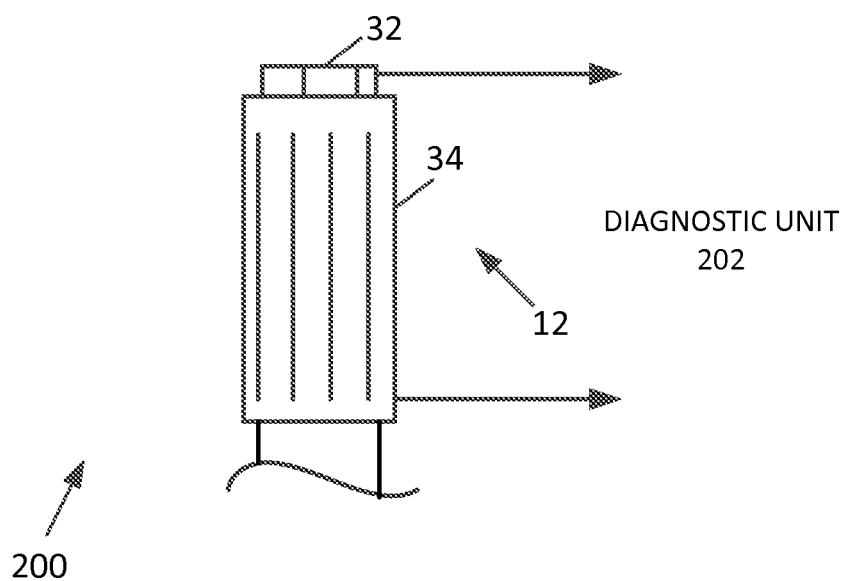
FIG. 6 is a generalized schematic view of a monitoring circuit integrated with the hose assembly of FIGS. 1-3.

FIG. 6 illustrates a general schematic view of an overall monitoring circuit 200 formed with the hose assembly 12, 112 to monitor abrasion of the hose 16. The monitoring circuit 200 includes the socket 34 and the nipple 32, and can be used to detect an electrical property of the hose assembly. For example, the monitoring circuit 200 may monitor electrical continuity between the conductive layer 24, 120, 124 and the nipple 32, thereby determining if electrical continuity exists between a conductive layer and a component external to the hose assembly 12, 112. In general monitoring circuit 200 is electrically connected to the diagnostic unit 14. The diagnostic unit 14 can be used, for example, to apply a stimulus to the monitoring circuit 200, and to derive an electrical characteristic for the hose assembly 12, 112. The stimulus may include at least one voltage so that the voltage is applied directly across the nipple 32 and the socket 34.

The diagnostic unit 14 may be adapted to the hose assembly 12, 112 in a variety of ways. For example, the diagnostic unit 14 may be included in such an exemplary monitoring assembly including housing and a circuit board as illustrated in U.S. patent application Ser. No. 13/458,691, the disclosure of which was previously incorporated by reference. The diagnostic unit 14 may have any of a variety of configurations depending on the electrical characteristic being monitored, such as resistance and capacitance. For example, the diagnostic unit 14 may include a sensing device 62 capable of measuring the desired electrical characteristic. The sensing device 62 may be electrically connected to the conductive layer 24, 120, 124 and the conductive component 54 by way of first and second lead wires 58, 60 (seen in FIGS. 1-3) that are electrically connected to the socket 34 and the nipple 32, respectively. Because the conductive layer 24, 120, 124 may also be connected to the socket 34, and the nipple 32 may also be connected to the conductive component 54, the diagnostic unit 14 may monitor electrical properties including electrical continuity of the overall monitoring circuit 200.

Figure 7:
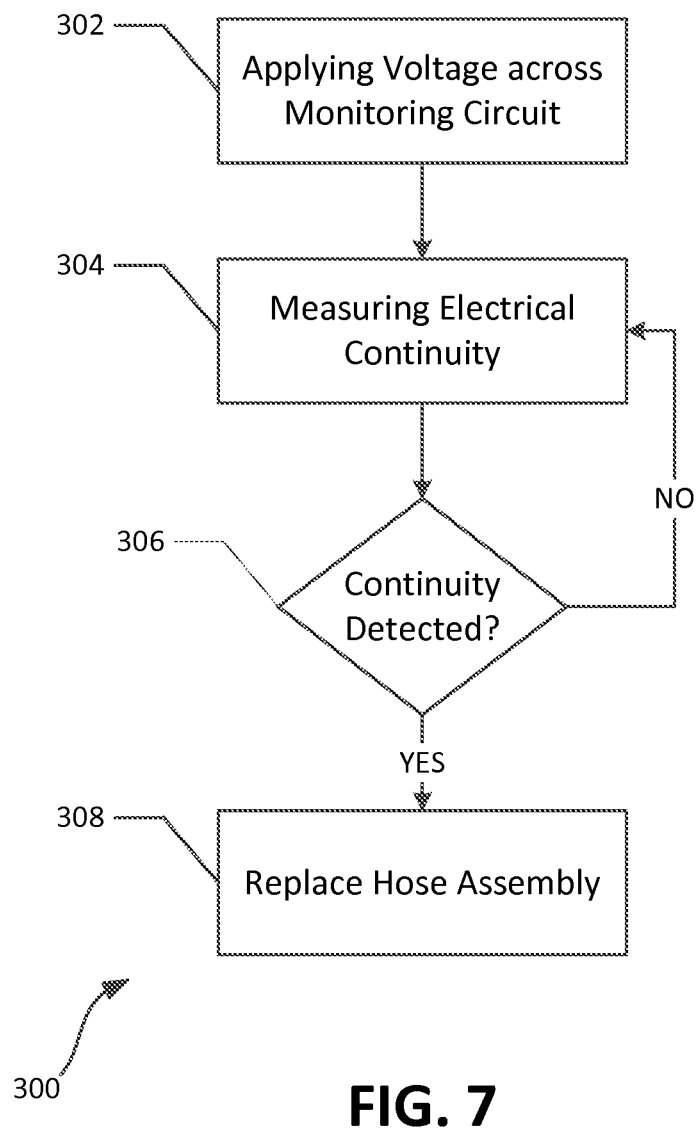
FIG. 7 is a flowchart of a method for monitoring abrasion of the hose assembly of FIGS. 1-3.

FIG. 7 is a representation of a method for monitoring abrasion of the hose assembly of FIGS. 1-3. The method 300 illustrates an example method for measuring an electrical characteristic of the hose assembly 12, 112 using the diagnostic unit 14.

According to the embodiment shown, an electrical signal (e.g., voltage or current) can be applied across the monitoring circuit 200, which consists of the hose assembly 12, 112, the diagnostic unit 14, and the component 54 (step 302). An electrical property of the monitoring circuit 200 can be determined (step 304) when the electrical signal is applied. The electrical property may include a total resistance of the monitoring circuit 200, or some other signal useable to detect electrical continuity between the nipple 32 and socket 34 (and therefore between a conductive portion of a component, such as surface 56 and an exposed conductive layer, such as layers 24, 120, 124). When no conductive layer 24, 120, 124, is exposed, the circuit 200 is substantially open, and the total resistance of the circuit 200 is substantially infinite. Therefore, the diagnostic unit 14 does not indicate electrical continuity of the monitoring circuit 200 (step 306). Steps 302-306, of applying a voltage across the monitoring circuit 200 and measuring the electrical property of the circuit 200, can be repeated periodically to provide substantially continuous monitoring of abrasion of the hose.

When the diagnostic unit 14 detects electrical continuity of the monitoring circuit 200 (step 306), the unit 14 may be configured to indicate that the hose assembly 12 should be replaced with a new one to prevent a complete failure of the hose 16 (step 308). This can occur in a variety of different ways, such as by activating a notification LED, generating an alarm signal or message, or other user-detectable feature.

Alternatively, or in addition to measuring electrical continuity of the monitoring circuit, a change in the electrical continuity of the monitoring circuit 200 may in some cases be measured to determine the degree of abrasion of the hose assembly 12, 112. In such cases, complete electrical continuity would not be required to indicate hose failure, but rather a change in the electrical property that is above a predetermined threshold may provide an indication of an impending failure.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A hose abrasion monitoring system comprising:
    a hose assembly including:
        a hose having at least one conductive layer and at least one outer insulating cover overlaying the at least one conductive layer; and
        a monitoring circuit in electrical communication with the at least one conductive layer;
        wherein the monitoring circuit is configured to detect electrical continuity between the at least one conductive layer, exposed by abrasion of the at least one outer insulating cover to expose a portion of the at least one conductive layer, and a conductive component external to the hose.

2. The hose abrasion monitoring system of claim 1, further comprising a diagnostic unit having a sensor measuring an electrical characteristic of a circuit formed at least partially from the at least one conductive layer.

3. The hose abrasion monitoring system of claim 2, wherein the diagnostic unit is configured to apply at least one voltage to the monitoring circuit to detect a resistance of the circuit.

4. The hose abrasion monitoring system of claim 1, further comprising a fitting for fluidly connecting the hose and a component.

5. The hose abrasion monitoring system of claim 4, wherein the fitting includes a socket and a nipple, and wherein the socket is electrically insulated from the nipple.

6. The hose abrasion monitoring system of claim 5, further comprising a collar disposed between the socket and the nipple, wherein the collar is configured to electrically isolate the nipple from the socket and the at least one conductive layer.

7. The hose abrasion monitoring system of claim 5, wherein the socket is electrically connected to the at least one conductive layer, and wherein the nipple is electrically connected to the component.

8. The hose abrasion monitoring system of claim 7, wherein the component has a conductive surface, wherein the monitoring circuit is electrically connected across the nipple and socket, and wherein the nipple is electrically connected to the conductive surface.

9. The hose abrasion monitoring system of claim 8, wherein the component is selected from a group of components consisting of:
   a vehicle bumper or guardrail;
   a trailer; and
   a metallic surface of a piece of hydraulic equipment.

10. The hose abrasion monitoring system of claim 1, wherein the at least one conductive layer includes an electrically conductive braided reinforcement material.

11. The hose abrasion monitoring system of claim 1, wherein the at least one conductive layer includes an electrically conductive spiral reinforcement material.

12. A method of monitoring abrasion of a hose assembly,
   applying a voltage across a monitoring circuit electrically connected between at least one conductive layer of the hose assembly and a conductive surface of a component, the at least one conductive layer being electrically insulated from the conductive surface; and
   measuring electrical continuity between the at least one conductive layer and the conductive surface.

13. The method of claim 12, further comprising detecting a change in the electrical continuity between the at least one conductive layer and the conductive surface.

14. The method of claim 12, wherein measuring electrical continuity between the at least one conductive layer and the conductive surface includes measuring an electrical characteristic of a circuit that includes the at least one conductive layer and the conductive surface.

15. The method of claim 12, wherein the hose is fluidly connected to the component.

16. The method of claim 12, wherein measuring electrical continuity comprises measuring electrical continuity between a socket and a nipple, wherein the at least one conductive layer is electrically connected to the socket, and the conductive surface is electrically connected to the nipple, the nipple being electrically insulated from the socket.

17. A hose abrasion monitoring system comprising:
   a hose assembly including a hose having a conductive layer and an outer insulating cover;
   a fitting for fluidly connecting the hose and a component, the component having a conductive surface, the fitting including:
      a socket electrically connected to the conductive layer; and
      a nipple electrically connected to the conductive surface, the nipple being electrically insulated from the socket;
   a monitoring circuit electrically connected between the nipple and the socket; and
   a diagnostic unit having a sensor measuring electrical continuity between the socket and the nipple, thereby measuring electrical continuity between the socket and the conductive surface.

18. The hose abrasion monitoring system of claim 17, wherein the hose includes a plurality of conductive layers.

19. The hose abrasion monitoring system of claim 18, wherein the hose includes one or more insulating layers separating each of the plurality of conductive layers.

20. The hose abrasion monitoring system of claim 17, further comprising a component having a conductive surface, and wherein the fitting is connected to the component thereby electrically connecting the nipple to the component, such that abrasion of the outer insulating cover by the conductive surface causes the conductive surface to contact the conductive layer, thereby creating electrical continuity between the conductive surface, the nipple, the socket, and the conductive layer.

* * * * *